(12) United States Patent
Ra et al.

(10) Patent No.: US 8,911,802 B2
(45) Date of Patent: Dec. 16, 2014

(54) **COMPOSITION FOR INCREASING MILK PRODUCTION CONTAINING *ARTEMISIA CAPILLARIS***

(71) Applicant: RNL BIO Co., Ltd., Seoul (KR)

(72) Inventors: Jeong Chan Ra, Gyeonggi-do (KR); Byeung Gie Kim, Gyeonggi-do (KR)

(73) Assignee: RNL BIO Co., Ltd., Seoul (KR)

( * ) Notice: Subject to any disclaimer, the term of this patent is extended or adjusted under 35 U.S.C. 154(b) by 0 days.

(21) Appl. No.: 13/678,159

(22) Filed: Nov. 15, 2012

(65) Prior Publication Data

US 2013/0071377 A1  Mar. 21, 2013

Related U.S. Application Data

(62) Division of application No. 12/668,571, filed on Jun. 15, 2010, now abandoned.

(30) Foreign Application Priority Data

Oct. 24, 2007  (KR) ........................ 10-2007-0107341

(51) Int. Cl.

| | | |
|---|---|---|
| *A61K 36/185* | (2006.01) | |
| *A61K 8/97* | (2006.01) | |
| *A61K 36/282* | (2006.01) | |
| *A61K 36/28* | (2006.01) | |
| *A23K 1/18* | (2006.01) | |
| *A23K 1/00* | (2006.01) | |
| *A23L 1/30* | (2006.01) | |

(52) U.S. Cl.
CPC .............. *A61K 36/282* (2013.01); *A23K 1/1813* (2013.01); *A23K 1/007* (2013.01); *A23L 1/3002* (2013.01)
USPC .......................................... 424/740; 424/725

(58) Field of Classification Search
CPC ............................... A23K 1/006; A23K 1/007
USPC ........................................................ 424/740
See application file for complete search history.

(56) References Cited

U.S. PATENT DOCUMENTS

2009/0068296 A1 * 3/2009 Greger .......................... 424/730

FOREIGN PATENT DOCUMENTS

| KR | 2003068240 A | * | 8/2003 |
| WO | WO 2006006768 A1 | * | 1/2006 |

* cited by examiner

*Primary Examiner* — Chris R Tate
*Assistant Examiner* — Deborah Davis
(74) *Attorney, Agent, or Firm* — Rabin & Berdo, P.C.

(57) ABSTRACT

The present invention relates to a composition for increasing the milk production of livestock, containing *Artemisia capillaris* as an active ingredient. More specifically, relates to a composition and a feed additive for increasing the milk production of cows, containing *Artemisia capillaris* as an active ingredient, and a composition and a feed additive for reducing the number of somatic cells in livestock milk, containing *Artemisia capillaris* as an active ingredient. The composition can increase milk production of animals, and, in addition, can reduce the number of somatic cells in milk being produces, thus enabling production of good quality milk.

4 Claims, No Drawings

COMPOSITION FOR INCREASING MILK PRODUCTION CONTAINING *ARTEMISIA CAPILLARIS*

CROSS-REFERENCE TO RELATED APPLICATIONS

This application is a divisional application of co-pending U.S. application Ser. No. 12/668,571, filed Jun. 15, 2010, the disclosure of which is incorporated herein by reference. This application claims priority benefits under 35 U.S.C. §119 to Korean Patent Application No. 10-2007-0107341 filed on Oct. 24, 2007, the disclosure of which is incorporated herein by reference in its entirety.

TECHNICAL FIELD

The present invention relates to a composition for increasing milk production of livestock, containing *Artemisia capillaris* as an active ingredient, and more particularly to a composition and a feed additive for increasing milk production of cows, containing *Artemisia capillaris* as an active ingredient, and to a composition and a feed additive for reducing the number of somatic cells in livestock milk, containing *Artemisia capillaris* as an active ingredient.

BACKGROUND ART

Growth hormones which are used in practice to increase milk production of dairy cows are known to have various physiological actions, including the promotion of cell growth, the promotion of protein production, the promotion of lipolysis and the stimulation of milk secretion in mammals. Human growth hormones were developed as products for promoting the growth of children, and animal growth hormones were developed as agents for increasing milk production of dairy cows, increasing the efficiency of pig feed and promoting the growth of cultured fishes.

As the utility of growth hormones exhibiting various physiological functions as described above draws attention, studies on substances or compositions for promoting the secretion of the growth hormones are being actively conducted. In addition, there is a need to study herbal compositions capable of increasing milk production by using herbal components to stimulate growth hormone secretion in dairy cows rather than agents for stimulating the secretion of growth hormone, comprising artificial chemical substances.

*Artemisia capillaries* Thunberg has been used as Chinese medicinal herb and is also called "Wormwood herb". *Artemisia* has various Korean names such as Kaae, Kucho, Kiae, Nangmihoja, Bingtae, Akeupae, Yayeundoo, Ae, Aebong, Aeho, Chumae, Chobong, Hyangae and Hwangcho.

The whole part of *Artemisia* contains components such as essential oil, tannin, resin, bitter substances, artemisinin, ascorbic acid and carotene, and the leaf thereof contains essential oil, cineole, thujone, borneol, paraffin, adenine, choline, vitamins A, B, and D, etc. The root of *Artemisia* contains polysaccharide artemos, essential oil, dehydromatricaric acid, sterol, tetradecatrien, inulin, mucus, etc.

*Artemisia* has a bitter and acrid taste, and also has warm nature and thus has the ability to disperse cold, stabilize the womb, regulate Qi and blood, expel dampness, warm the uterus, promote bile secretion, invigorate blood, stop bleeding, relieve pain, eliminate blood stasis, regulate menstruation, and restore yang. Thus, *artemisia* is used to alleviate and treat abdominal cold-pain, abdominal cramps caused by diarrhea, chronic diarrhea and dysentery, spitting blood, nasal bleeding, vaginal bleeding, menstrual irregularity, abnormal uterine bleeding, vaginal discharge, fetal irritability, and tumor.

Accordingly, the present inventors have found that, when *Artemisia capillaris* powder, *Artemisia capillaris* extract or fermented *Artemisia capillaris* is fed to dairy cows, milk production of the cows can be increased, and the number of somatic cells in raw milk being produced can be decreased which will enable the cows to produce good-quality milk, thereby completing the present invention.

SUMMARY OF INVENTION

It is an object of the present invention to provide a composition for increasing milk production of livestock, a composition for promoting human breast milk production, and a composition for reducing somatic cells in livestock, each of the compositions containing *Artemisia capillaries* as an active ingredient.

To achieve the above object, the present invention provides a composition and a feed additive for increasing milk production of livestock, containing *Artemisia capillaris* as an active ingredient.

The present invention also provides a composition for promoting human breast milk production, containing *Artemisia capillaris* as an active ingredient.

Other features and aspects of the present invention will be apparent from the following detailed description and the appended claims.

DETAILED DESCRIPTION OF THE INVENTION, AND PREFERRED EMBODIMENTS

In one aspect, the present invention relates to a composition and a feed additive for increasing milk production of livestock, containing *Artemisia capillaris* as an active ingredient.

In the present invention, the *Artemisia capillaris* is preferably selected from the group consisting of *Artemisia capillaris* powder, *Artemisia capillaris* extract and fermented *Artemisia capillaris*. In the present invention, the *Artemisia capillaris* powder may be prepared by drying *Artemisia capillaires* Thunberg at suitable temperature, finely cutting the dried material, and then grinding the cut material to a size of 20-100 mesh, the *Artemisia capillaris* extract may be prepared by extracting the *Artemisia capillaris* powder with ethanol and drying the extract, and the fermented *Artemisia capillaris* may be prepared by mixing the *Artemisia capillaris* powder with rice barn and the like, adding a fermentation starter and lactic acid bacteria thereto to ferment the *Artemisia capillaris* powder, drying the fermented material to a water content of 13-15%, thus preparing fermented *Artemisia capillaris* powder, and then adding a pharmaceutically acceptable carrier.

The *Artemisia capillaris* powder of the present invention may be mixed with a suitable carrier such as alfalfa at a weight ratio of 18-36:82-67 before use, and the *Artemisia capillaris* extract may be mixed with a suitable carrier such as alfalfa at a weight ratio of 1.6-7.2:9.4-13.8 before use.

In a preferred embodiment, the fermented *Artemisia capillaris* of the present invention may be prepared by mixing 18-36 wt % of *Artemisia capillaris* powder with 82-64 wt % of rice bran mixture (wheat powder, corn flour, zeolite, etc.), adding a fermentation starter (yeast), various lactic acid bacteria and a suitable carrier thereto, fermenting the mixture for 3-7 days and drying the fermented material.

Thus, in the present invention, the *Artemisia capillaris* extract, the *Artemisia capillaris* powder and the fermented

*Artemisia capillaris* powder may be added to a conventional compound feed comprising corn, soybean meal, wheat, tallow, molasses, calcium phosphate, limestone, salt, other minerals, and a vitamin premix in a suitable amount. Preferably, each of the *Artemisia capillaris* extract, the *Artemisia capillaris* powder and the fermented *Artemisia capillaris* powder is preferably added in an amount of 0.005-50 wt % based on the total weight of feed in order to obtain the desired effect of increasing milk production in livestock.

In the present invention, the livestock are preferably selected from the group consisting of cattle, dairy cattle, sheep, mountain sheep, goats, pigs, horses, camels and dogs. More preferably, the livestock are dairy cattle or mountain sheep.

In another aspect, the present invention relates to a composition for promoting human breast milk production, containing *Artemisia capillaris* as an active ingredient.

The composition may be administrated in the form of a pharmaceutical formulation or a functional food.

The inventive composition containing *Artemisia capillaris* as an active ingredient can reduce the number of somatic cells in raw milk produced by livestock, thus enabling production of good quality milk.

Accordingly, the present invention relates, in another aspect, to a composition and a feed additive for reducing somatic cells in livestock milk, containing *Artemisia capillaris* as an active ingredient.

The composition of the present invention may be prepared into a given formulation according to a conventional method. In the preparation of the formulation, it is preferable that *Artemisia capillaris* or fermented *Artemisia capillaris* as an active ingredient be mixed or diluted with a carrier, or encapsulated in a capsule-shaped carrier.

If the carrier is used as a diluent, it may be solid, semi-solid or liquid substance acting as a vehicle, excipient or medium for the active ingredients. Thus, the formulation may be in the form of tablets, pills, powder, sachet, elixir, suspension, emulsion, solution, syrup, aerosol, soft or hard gelatin capsules, sterilize injectable solution and sterilize powder. The formulation may additionally comprise fillers, anti-aggregating agents, lubricants, wetting agents, perfumes, emulsifiers, preservatives and the like. The pharmaceutical composition according to the present invention may be formulated using a method well known in the art, such that it can provide the rapid, sustained or delayed release of the active ingredient after administration.

The *Artemisia capillaris* extract, the *Artemisia capillaris* powder or the fermented *Artemisia capillaris* powder as an active ingredient may be administered orally or parentarally to animals, including humans, in an amount of 10-1,000 mg/kg of body weight, preferably 70-100 mg/kg of body weight, in single or multiple daily doses. For dairy cattle, the composition of the present invention may be mixed with feed in an amount of 1-50 wt % before feeding or may be fed at a dose of 5-100 g/day/animal.

EXAMPLES

Hereinafter, the present will be described in further detail with reference to examples. It is to be understood, however, that these examples are for illustrative purposes only and are not to be constructed to limit the scope of the present invention.

Example 1

Preparation of *Artemisia capillaris* Powder, *Artemisia capillaris* Extract Powder and Fermented *Artemisia capillaris*

(1) Preparation of *Artemisia capillaris* Powder

*Artemisia capillaris* was dried in a dryer to a water content of about 10%. Then, the dried plant was finely cut to a size of 1.5-2 cm, and then ground in a grinder in two steps to a particle size of 20-80 mesh. The resulting *Artemisia capillaris* powder was mixed with alfalfa as a carrier at a weight ratio of 18:82, thus preparing *Artemisia capillaris* powder.

(2) Preparation of *Artemisia capillaris* Extract Powder

*Artemisia capillaris* was placed in a dryer and dried to a water content of about 10%. Then, the dried plant was finely cut to a size of 1.5-2 cm, and the cut plant was extracted with ethanol in an extractor. The extract was dried and ground to fine powder, and the *Artemisia capillaris* was mixed with alfalfa as a carrier at a weight ratio of 1.8:98.2, thus preparing *Artemisia capillaris* extract powder.

(3) Preparation of Fermented *Artemisia capillaris*

18 wt % of the *Artemisia capillaris* powder prepared in Example 1-(1) was mixed with 82 wt % of rice bran mixture (wheat powder, corn flour, zeolite, etc.), and then mixed with a fermentation starter (yeast) and various lactic bacteria at a weight ratio of *Artemisia capillaris* powder/rice bran mixture: fermentation starter/lactic bacteria=99.95:0.05. The mixture was fermented for 3-7 days and dried, thus preparing fermented *Artemisia capillaries*.

Example 2

Measurement of Change in Milk Production of Dairy Cows According to Administration of Fermented *Artemisia capillaris*

As test subjects, Holstein dairy cows ($1^{st}$ to $6^{th}$ parity) at 45-280 days after delivery were divided into three groups: a group fed with *Artemisia capillaris*, and two control groups, each of the groups consisting of 10 cows. For the test group, the fermented *Artemisia capillaris* (contained in a formulation in an amount of 18 wt %) was administered to each individual at the time of milking in an amount of 10 g per cow. For the positive control group, 500 mg of sustained-release recombinant bovine somatotropin (BST, LG Life Sciences Ltd.) was subcutaneously injected into an alternately selected one of the right and left sides of the ischiorectal fossa at two-week intervals. The amount of concentrate feed was adjusted depending on milk yield, the animals were allowed free access to forage, and other raising conditions followed the usual practice of the test farm. At the start and end of the test, each of the groups was measured for milk production and calculated for the rate of an increase in milk production.

As a result, as can be seen in Table 1, the group fed with fermented *Artemisia capillaris* showed a milk production increase of about 17% for 8 weeks, suggesting that the milk production thereof was higher than that of the group fed with somatotropin.

TABLE 1

Unit: daily average milk production (kg) per cow

|  | Fermented Artemisia capillaris | Negative control | Positive control |
|---|---|---|---|
| Milk production at the start (kg) | 30.5 | 32.2 | 31.2 |
| Milk production at the end (kg) | 35.7 | 32.1 | 35.9 |
| Increase rate in milk production (%) | 17 | −0.3 | 15 |

Example 3

Measurement of Change in Milk Production of Dairy Cows According to the Kind of *Artemisia capillaris* Fed As test subjects, Holstein dairy cows ($1^{st}$ to $5^{th}$ parity) at 50-280 days after delivery were divided into three groups fed with *Artemisia capillaris*, and a control group, each of the groups consisting of 10 cows. The *Artemisia capillaris* powder (contained in a formulation in an amount of 18 wt %), the *Artemisia capillaris* extract powder (contained in a formulation in an amount of 3.6 wt %) and the fermented *Artemisia capillaris* (contained in a formulation in an amount of 18 wt %) were fed to the respective groups in an amount of 10 g per cow. The amount of feed to the control group was adjusted depending on the content of a mixed feed, the animals were allowed free access to forage, and other raising conditions followed the usual practice of the test farm. At the start and end of the test, each of the groups was measured for milk production and calculated for the rate of the increase in milk production.

As a result, as can be seen in Table 2 below, the control group showed no significant change in milk production, whereas the group fed with the fermented *Artemisia capillaris* showed a milk production increase of 4.5 kg for 16 weeks, which corresponded to an increase of 13.2% compared to milk production before administration, and the *Artemisia capillaris* extract-fed group and the *Artemisia capillaris* powder-fed group showed milk production increase of 3.3 kg and 3.9 kg, respectively, which corresponded to increase of 9.4% and 11.4% compared to milk production before administration.

TABLE 2

Unit: daily average milk production (kg) per cow

|  | Artemisia capillaris powder | Artemisia capillaris extract | Fermented Artemisia capillaris | Negative control |
|---|---|---|---|---|
| Milk production at the start (kg) | 35.2 | 34.3 | 34.2 | 35.8 |
| Milk production at the end (kg) | 38.5 | 38.2 | 38.7 | 35.9 |
| Increase rate in milk production (%) | 9.4 | 11.4 | 13.2 | 0.3 |

Example 4

Measurement of Change in Number of Somatic Cells in Raw Milk According to Administration of *Artemisia capillaris*

As test subjects, Holstein dairy cows ($1^{st}$ to $5^{th}$ parity) at 47-279 days after delivery were divided into a non-fed control group, three groups fed with *Artemisia capillaris*, and a positive control group, each of the groups consisting of 10 cows. For the groups fed with *Artemisia capillaris*, each of the *Artemisia capillaris* powder (contained in a formulation in an amount of 18 wt %), the *Artemisia capillaris* extract (contained in a formulation in an amount of 3.6 wt %) and the fermented *Artemisia capillaris* (contained in a formulation in an amount of 18 wt %) was fed in an amount of 10 g/day/cow.

The amount of feed to the control group was adjusted depending on the content of a mixed feed, the animals were allowed free access to forage, and other raising conditions followed the usual practice of the test farm. At the start, middle and end of the test, each of the groups was measured for somatic cells. Somatic cell count (SCC) was analyzed using a somatic cell counter (Fossomatic 300, Denmark).

As a result, as can be seen in Table 3, the non-fed group showed no significant change in milk production, whereas, in the group fed with the fermented *Artemisia capillaris*, the number of somatic cells was decreased from 470,000 cells/ml of raw milk to 190,000 cells/ml of raw milk for 16 weeks. The number of somatic cells was decreased from 450,000 cells/ml to 240,000 cells/ml for 16 weeks for the group fed with *Artemisia capillaris* extract powder and from 480,000 cells/ml to 220,000 cells/ml for 16 weeks for the group fed with the *Artemisia capillaris* powder.

TABLE 3

Unit: cells/ml of raw milk

| Number of somatic cells | Artemisia capillaris powder | Artemisia capillaris extract | Fermented Artemisia capillaris | Negative control |
|---|---|---|---|---|
| At the start | 450,000 | 480,000 | 470,000 | 450,000 |
| After 4 weeks | 410,000 | 430,000 | 420,000 | 440,000 |
| After 8 weeks | 350,000 | 340,000 | 300,000 | 430,000 |
| After 16 weeks | 240,000 | 220,000 | 190,000 | 430,000 |

INDUSTRIAL APPLICABILITY

As described in detail above, the composition according to the present invention can increase milk production of animals, including humans, and, in addition, can reduce the number of somatic cells in milk being produced, thus enabling production of good quality milk.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for increasing milk production of livestock, said method comprising administering an effective amount of a feed additive consisting essentially of fermented *Artemisia capillaris* as an active ingredient to said livestock resulting in an average increase in milk production from 13.2% to 17%.

2. A method for increasing milk production of livestock, said method comprising administering and effective amount of a composition consisting essentially of fermented *Artemisia capillaris* as an active ingredient to said livestock resulting in an average increase in milk production from 13.2% to 17%.

3. A method for reducing somatic cells in livestock milk, said method comprising administering an effective amount of a composition consisting essentially of fermented *Artemisia*

*capillaris* as an active ingredient to said livestock resulting in an average decrease in the number of somatic cells from 10.7% to 59.6%.

4. A method for reducing somatic cells in livestock milk, said method comprising administering an effective amount of a feed additive consisting essentially of fermented *Artemisia capillaris* as an active ingredient to said livestock resulting in an average decrease in the number of somatic cells from 10.7% to 59.6%.

* * * * *